United States Patent
Bernhardt et al.

(10) Patent No.: US 10,307,127 B2
(45) Date of Patent: Jun. 4, 2019

(54) CORRECTING X-RAY IMAGE DATA RELATING TO A DECAY PROCESS OF A RADIOACTIVE MATERIAL

(71) Applicants: Philipp Bernhardt, Forchheim (DE); Dirk Ertel, Forchheim (DE); Michael Stark, Forchheim (DE)

(72) Inventors: Philipp Bernhardt, Forchheim (DE); Dirk Ertel, Forchheim (DE); Michael Stark, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 331 days.

(21) Appl. No.: 15/258,296

(22) Filed: Sep. 7, 2016

(65) Prior Publication Data
US 2017/0071561 A1    Mar. 16, 2017

(30) Foreign Application Priority Data
Sep. 15, 2015    (DE) .................. 10 2015 217 617

(51) Int. Cl.
*A61B 6/00* (2006.01)
*A61N 5/10* (2006.01)
(Continued)

(52) U.S. Cl.
CPC ............ *A61B 6/5205* (2013.01); *A61B 6/032* (2013.01); *A61B 6/4241* (2013.01);
(Continued)

(58) Field of Classification Search
CPC ..... A61B 6/032; A61B 6/4241; A61B 6/4258; A61B 6/4441; A61B 6/5205; A61B 5/055;
(Continued)

(56) References Cited

U.S. PATENT DOCUMENTS

| 7,348,564 | B2 * | 3/2008 | Wollenweber ......... A61B 6/032 250/363.02 |
| 2004/0096036 | A1 * | 5/2004 | Yanoff ................. A61B 6/5235 378/98.8 |

(Continued)

FOREIGN PATENT DOCUMENTS

| DE | 102005054575 B3 | 4/2007 |
| DE | 102005053994A1 A1 | 5/2007 |

(Continued)

OTHER PUBLICATIONS

Fei, Baowei, et al. "The safety issues of medical robotics." Reliability Engineering & System Safety 73.2 (2001):183-192.
(Continued)

*Primary Examiner* — Irakli Kiknadze
(74) *Attorney, Agent, or Firm* — Lempia Summerfield Katz LLC

(57) ABSTRACT

X-ray image data of an examination subject is acquired for an acquisition period by an X-ray detector of an X-ray system simultaneously with a decay process of a radioactive material taking place in or on the examination subject. The X-ray image data includes information relating to an X-ray attenuation distribution of the examination subject and information relating to the decay process. Correction image data representing the information relating to the decay process in the X-ray image data for the acquisition period is determined. Corrected X-ray image data for the acquisition period is generated using the X-ray image data and the correction image data.

20 Claims, 4 Drawing Sheets

(51) Int. Cl.
*A61B 6/03* (2006.01)
*G01N 23/04* (2018.01)

(52) U.S. Cl.
CPC .......... *A61B 6/4258* (2013.01); *A61B 6/4441* (2013.01); *A61N 5/10* (2013.01); *A61N 5/1049* (2013.01); *A61N 5/1001* (2013.01); *A61N 2005/1061* (2013.01)

(58) Field of Classification Search
CPC ..... A61B 6/037; A61B 5/0205; A61B 5/7289; A61B 6/0478; A61B 6/107; A61B 6/4057; A61B 6/4423; A61B 6/507; A61B 6/508; A61B 6/5288; A61B 6/548; A61B 6/583; A61B 5/415; A61B 5/418; A61B 6/4291; A61B 5/4076; A61B 5/417; A61B 6/467; A61B 6/501; A61N 2005/1061; A61N 5/10; A61N 5/1001; A61N 5/1049; G01N 2223/419; G01N 2223/505; G01N 23/046; G01N 2223/108; G01N 23/2255; G01N 2223/04; G01N 2223/05; G01N 2223/071; G01N 2223/0745; G01N 2223/1006; G01N 2223/40; G01N 2223/402; G01N 2223/501; G01N 2223/639; G01N 23/02
USPC .............. 378/62, 63, 64, 21, 65; 702/57, 15; 250/363.04
See application file for complete search history.

(56) References Cited

U.S. PATENT DOCUMENTS

| | | | |
|---|---|---|---|
| 2005/0238139 | A1* | 10/2005 | Gipp ........................ A61B 6/00 378/97 |
| 2007/0013336 | A1 | 1/2007 | Nowlin et al. |
| 2007/0102645 | A1* | 5/2007 | Maschke ................ G01T 1/1615 250/370.09 |
| 2007/0120512 | A1 | 5/2007 | Albu-Schaffer et al. |
| 2008/0230705 | A1* | 9/2008 | Rousso ................... A61B 5/415 250/363.04 |
| 2008/0240366 | A1* | 10/2008 | Bacher ..................... H04N 5/32 378/207 |
| 2010/0010757 | A1* | 1/2010 | Schmidt ................. A61B 6/037 702/57 |

FOREIGN PATENT DOCUMENTS

| | | |
|---|---|---|
| DE | 102012015975 A1 | 3/2013 |
| WO | WO2004095069A1 A1 | 11/2004 |

OTHER PUBLICATIONS

German Office Action for German Application No. 102014224123.5, dated Aug. 4, 2015, with English Translation.
German office Action for related German Application No. 10 2015 217 617.7 dated Apr. 19, 2016, with English Translation.
Spahn Martin, "Flat detectors and their clinical applications",in: European Radiology, vol. 15, pp. 1934-1947, 2005, DOI:10.1007/s00330-005-2734-9.

* cited by examiner

CORRECTING X-RAY IMAGE DATA RELATING TO A DECAY PROCESS OF A RADIOACTIVE MATERIAL

RELATED CASE

This application claims the benefit of DE 102015217617.7, filed on Sep. 15, 2015, which is hereby incorporated by reference in its entirety.

FILED

The embodiments relate to a method for correcting X-ray image data of an examination subject that is acquired for an acquisition period by an X-ray detector of an X-ray system simultaneously with a decay process of a radioactive material taking place in or on the examination subject. The embodiments also relate to a corresponding computer program, a corresponding data medium, a corresponding data processing device, and a corresponding X-ray system.

BACKGROUND

Current-generation X-ray detector technology permits excellent medical imaging. Even at an X-ray dose that is advantageously low for the patient, it is possible to generate an X-ray image dataset providing acceptable image quality. This is attributable above all to a constant improvement in quantum efficiency or, as the case may be, a constant improvement in absorption properties of the X-ray detectors. For specific medical application scenarios, this improvement in detector sensitivity may also lead to negative effects on image quality. A possible problematic application case occurs when an examination subject, in particular a patient, is to be examined by X-ray imaging while at the same time a radioactive decay process is taking place in or on the body of the examination subject. This decay process generates gamma radiation. Whereas X-ray radiation denotes ionizing radiation in the form of electromagnetic waves having quantum energies between 5 keV and several 100 keV, ionizing radiation in the form of electromagnetic waves having quantum energies of more than 40 keV, typically 140 keV, is described as gamma radiation. If an X-ray examination and a radioactive decay process are in progress simultaneously in immediate spatial proximity, the X-ray detector detects not only the X-ray quanta but also the gamma radiation of the radioactive decay. The gamma radiation is superimposed as an unwanted interfering signal on the actually wanted X-ray signal. It is particularly problematic in this regard if there is an at least partial spectral overlap between the gamma radiation and the X-ray radiation. In application situations of this type, such as occur for example in brachytherapy when a radioactive substance intended for local tumor treatment is applied to a patient or its position in or on the body of the patient is to be checked subsequently, the consequence at the present time is a degradation, in some cases considerable, in image quality with regard to the diagnostic relevance of the X-ray image dataset in relation to the determined X-ray attenuation distribution.

SUMMARY AND DETAILED DESCRIPTION

Against this background, it is the object of the present embodiments to provide X-ray image datasets that have a comparatively reduced interfering signal that is attributable to the radioactive decay and as a result possess an improved image quality.

This object is achieved by a method for correcting X-ray image data of an examination subject, as well as by a corresponding computer program, a data medium, a data processing device and an X-ray system.

Features, advantages or alternative embodiments mentioned are equally to be applied also to the other subject matters, and vice versa. In other words, object-related embodiments (which are directed to a method, for example) can also be developed by features that are described in connection with a device. The corresponding functional features of the method are in this case embodied by corresponding object-related modules or units.

The embodiments relate to a method for correcting X-ray image data of an examination subject. Said X-ray image data is acquired for an acquisition period by an X-ray detector of an X-ray system. At the same time, however, a decay process of a radioactive material is taking place in or on the examination subject. This decay process is characterized by the emission of gamma quanta, which can likewise be detected by the X-ray detector. Accordingly, the X-ray image data include information relating to an X-ray attenuation distribution of the examination subject and information relating to the decay process. The method according to the an embodiment includes the following steps:
  determining correction image data representing the information relating to the decay process in the X-ray image data for the acquisition period, and
  generating corrected X-ray image data for the acquisition period using the X-ray image data and the correction image data.

The embodiment is based on the knowledge that the quality of the X-ray image data, which is detrimentally affected by the information relating to the decay process to the extent that said information distorts the impression of the X-ray attenuation distribution of the examination subject, can be improved by correcting the X-ray image data by correction image data representing the information relating to the decay process. In other words, X-ray image data is generated in which the information content in relation to the decay process is reduced or from which the information relating to the decay process is eliminated.

The X-ray image data is obtained in the course of an irradiation of the examination subject with X-ray radiation. In this case, an X-ray detector acquires the X-ray image data in the form of at least one X-ray projection in at least one defined spatial direction. To that end, the X-ray detector detects spatially resolved incident radiation in the sensitive spectral range and adds together all count events within an acquisition period. The spatially resolved count information for the acquisition period is subsequently used for reconstructing the X-ray image data. The duration of an acquisition period is dependent firstly on the body region under investigation of the examination subject, in particular a patient, or on a planned type of examination and is determined further by the X-ray system being used therefor.

The method according to an embodiment can be employed in any X-ray system, for example in C-arm systems, in angiography systems, in conventional X-ray systems, in mammography systems, in systems for interventional radiography or in computed tomography systems.

Typical values for the duration of an acquisition period are e.g. 10 ms for angiography or 0.25 ms for computed tomography, wherein, in the case of computed tomography also, an acquisition period relates to the acquisition of an X-ray projection in a defined spatial direction. The acquisition period can also include the acquisition of more than one projection, e.g. an acquisition period can include the acquisition of projections and, in the case of computed tomography in particular, in a plurality of projection directions.

The X-ray projection represents the distribution of the X-ray attenuation caused by the irradiated body part in the projection direction. Due to the radioactive decay taking place in or on the examination subject at the same time as the acquisition of X-ray image data, the X-ray attenuation distribution is overlaid by likewise detected gamma quanta of the radioactive decay process.

The radioactive material can be present in the body or on the body, i.e. close to the surface of the body of the examination subject, as is the case e.g., in local radiation therapy, also known as brachytherapy, primarily for the treatment of tumors. Other applications or situations in which a radioactive decay process takes place in or on the examination subject are also conceivable, e.g., radiation accidents, incidents of poisoning, etc. Radionuclides preferably employed in brachytherapy and causing gamma radiation are e.g., cesium-137, cobalt-60, iridium-192, iodine-125 or palladium-103.

The correction image data according to an embodiment is determined in such a way that the correction image data provides an indication of the radioactive decay taking place in or on the examination subject. In other words, the correction image data represents a signal component in the X-ray image data caused by the radioactive decay and corresponding to an interfering signal. The correction image data can then be applied to or computed with the X-ray image data in order to reduce or remove the interfering signal from the X-ray image data. Accordingly, corrected X-ray image data is generated that, aside from image errors or artifacts from other sources, represents a more realistic mapping of the X-ray attenuation distribution of the examination subject. The correction image data is preferably subtracted from the X-ray image data. This operation can also be a weighted subtraction in which the correction image data is e.g., first multiplied with a weighting factor. Preferably, the computation is performed image element by image element, that is to say pixel by pixel for two-dimensional image data or voxel by voxel for three-dimensional image data.

Both the X-ray image data and the correction image data can be three-dimensional or two-dimensional image data. Two-dimensional correction image data can also be determined e.g., by two-dimensional projection of a three-dimensional correction volume.

In a development, the correction image data is determined for a time window that precedes and/or is concurrent with the acquisition period. A correction of the X-ray image data is carried out most effectively when the correction image data is determined for a time period that is identical with, has overlaps with or at least is separated by only a slight temporal distance from the acquisition period for the X-ray image data. The decay activity is subject to a physical law according to which the decay activity decreases exponentially with time. To that extent, a meaningful correction of the X-ray image data can only be carried out with correction data that represents the decay process of the radioactive material at or close to the time instant or over the time period of the acquisition of the X-ray image data.

In an advantageous embodiment, the time window precedes the acquisition period and has a multiple of the length of the acquisition period. The signal component included in the X-ray image data and attributable to the decay process is assumed to be relatively small (which, at least locally, can nonetheless lead to considerable losses in image quality with regard to the X-ray attenuation distribution). By considering the correction image data over an extended time window compared to the acquisition period, it is advantageously possible to reduce the expected relative noise component in the correction image data while at the same time increasing relevance of the correction image data, without in the process reducing the temporal correlation between acquisition time of the X-ray image data and determination of the correction image data.

In an advantageous development, the time window lies between two successive acquisition periods. This and also the previous development take account of the fact that C-arm X-ray systems in particular are used for a repeated X-ray image acquisition, for which X-ray projections are acquired at fixed time intervals, e.g., in perfusion measurements or in cardiac angiography, etc. In this case, pulsed X-ray radiation can also be used, e.g., at a pulse frequency of 10 Hz. The duration of an acquisition period, e.g., 10 ms, is usually significantly shorter than the repetition time (frame rate) for recording an X-ray projection, in this case 100 ms. To that extent, a time window having a multiple of the length of an acquisition period is produced between two successive acquisition periods. On the one hand, said time window, which is present in any case between the acquisitions, can now be used for determining correction image data without the need for any additional time investment. On the other hand, said time window has a sufficient length or duration to allow unwanted noise to be eliminated from the correction image data. Furthermore, owing to the time window being arranged in each case between two acquisition periods, an excellent temporal relationship is ensured between X-ray image data and correction image data.

In a further embodiment, the determining of the correction image data includes an acquisition of decay image data by the X-ray detector. The decay image data can be acquired during the acquisition period and/or outside thereof. Preferably, the decay image data is acquired within the time window. The decay image data represents the radiation detected by the X-ray detector and caused by the radioactive decay. If the X-ray image data is acquired outside of the acquisition period, no X-ray radiation is emitted in parallel by a radiation source, at least in applications employing pulsed X-ray radiation. Apart from noise effects, radiation impinging on the detector can be assigned unequivocally to the decay process. If X-ray image data acquisition and decay image data acquisition are performed at least partially concurrently or if X-ray radiation is emitted continuously during the decay image data acquisition, such as e.g., in the case of a computed tomography examination, the detected radiation must be separated into a signal component representing the X-ray attenuation distribution and a signal component representing the decay process at least for the overlapping time in order to determine the decay image data. This can be accomplished e.g., by an evaluation of the energy spectrum of the incident radiation. Thus, in the case of the signal component representing the X-ray attenuation, a continuous spectrum having substantially known energy distribution can be assumed. The X-ray spectrum is generally composed of a continuous bremsstrahlung spectrum and K lines ($\alpha$, $\beta$ edges) characteristic of the anode material used. The maximum energy of the spectrum is in this case determined by the acceleration voltage. In contrast, the spectrum of the radioactive decay is discrete. The separation proves to be particularly simple when the two signal components have no spectral overlap.

In an advantageous development, the determining of the correction image data includes an acquisition of decay image data by the X-ray detector over the entire duration of the time window. The larger the time window, the more effectively the noise in the decay image data can be eliminated. Within the time window, a plurality of individual decay projections can be acquired, wherein the X-ray detector adds together events for a decay projection, e.g., in each case over the duration of the acquisition period. In this way, the embodiment can be realized in a particularly simple manner while maintaining the cycle time of the detector. Alternatively, it is also possible to acquire only one decay image for the entire duration of the time window, the X-ray detector in this case integrating count signals over the entire time window. The readout time of the X-ray detector for transmitting the spatially resolved count signals to the peripherals, during which the detector is insensitive to incident radiation, can be advantageously excluded from the time window.

In a further embodiment variant of the method, the decay image data is normalized to the duration of the acquisition period in order to determine the correction image data. This approach is a product of the consideration that the correction image data not only optimally represents the actual decay process of the radioactive material by the fact that the correction image data and X-ray image data have a close temporal relationship, but also by the fact that the correction image data is determined for exactly the same duration as the acquisition period. Various computational operations can be applied to the decay image data for the normalization, these being dependent in the individual case on the type of decay image data. For example, in the case of decay image data in the form of a plurality of individual projections having a length greater than the duration of the acquisition period, a noise-reducing averaging of the decay projections can be performed initially, wherein the averaging can be performed over the signal contents of the individual projections for each image element. A reduction of the signal contents can then be performed for each image element, more specifically as a function of the ratio of the duration of the acquisition period to the time period for recording a respective individual projection.

According to another development, the characteristic energy spectrum of the decay process of the radioactive material is taken into account during the acquisition of the decay image data. The decay process of the radioactive material generally takes place at a discrete quantum energy, whereas the expected spectrum of the X-ray quanta incident on the X-ray detector runs continuously, possibly with known peak energies. These spectral properties can be useful in multiple ways for the acquisition of the decay image data. On the one hand, noise-induced count signals can be excluded from the decay image data already during the acquisition of the decay image data by the X-ray image detector. On the other hand, taking the spectral properties into account facilitates the acquisition of decay image data simultaneously with the acquisition of X-ray image data, as a result of which an optimal temporal correlation between the correction image data and the X-ray image data can be achieved. In this development, the X-ray detector is advantageously embodied as an energy-selective X-ray detector, as is described in detail further below.

In a further embodiment, the correction image data is determined taking into account the characteristic course of the decay process for the radioactive material. In particular for the case in which X-ray image data is acquired repeatedly during an examination of an examination subject by X-ray radiation at fixed time intervals over a fixed acquisition period in each case while maintaining the projection angle, such as is the case in angiography, for example, better correction image data can be determined by taking into account the characteristic course of the decay process. The start time of the decay of the radioactive material in or on the examination subject is generally known. It is also generally known which radioactive material is involved. From the temporal relationship between start time of the decay process and start times of the individual acquisition periods or of the individual time windows, it is possible to align the correction image data to a time characteristic corresponding to the characteristic decay process. For example, the noise-polluted decay image data acquired during a plurality of time windows can be fitted to the characteristic decay process. Alternatively, a measure for the deviation of expected decay signal from actually measured decay signal can be determined, which measure is then taken into account in the computation of the X-ray image data with the associated correction image data, e.g., in the form of a weighting factor as already mentioned above.

In another development, the method also includes determining a distribution of the radioactive material on or in the examination subject on the basis of the decay image data or the correction image data. This stems from the recognition that the correction image data or, as the case may be, the decay image data that for the previous method was considered simply as an interfering signal requiring to be eliminated, likewise contains image information. This can be used to visualize the distribution in the tissue or, as the case may be, the enhancement of the tissue of the examination subject with the radioactive material. To that end, for example for a repeated acquisition of X-ray images as already described above, it is possible, while maintaining the projection direction, to consider each acquired individual projection of the decay image data or differential projections from succeeding time windows (particularly advantageous when a time characteristic of the enhancement or distribution of the radioactive material is to be represented). By averaging a plurality of individual projections, including projections further removed in time, it is in turn possible to achieve an improved image impression as a result of noise suppression.

In another embodiment, a computer program includes program code for performing all method steps when the program is executed in a computer. This renders the method reproducible and capable of being performed on different computer with little susceptibility to error.

In yet another embodiment, a machine-readable data medium on which the previously described computer program is stored is provided.

Furthermore, an embodiment relates to a data processing device for correcting X-ray image data of an examination subject, which data is acquired for an acquisition period by an X-ray detector of an X-ray system at the same time as a decay process of a radioactive material taking place in or on the examination subject. In this case, the X-ray image data includes information relating to an X-ray attenuation distribution of the examination subject and information relating to the decay process. The data processing device is configured for determining correction image data representing the information relating to the decay process in the X-ray image data for the acquisition period, and generating corrected X-ray image data for the acquisition period using the X-ray image data and the correction image data.

What is generally to be understood by the term data processing device is a computer or a plurality of computers engaging in data exchange with one another, each including at least one processor. The data processing device can be embodied as part of an X-ray detector or as part of an X-ray system. As part of the X-ray detector, the data processing device can be part of the peripherals. As part of the X-ray system, the data processing device can be embodied as part of the control unit or the computing unit or be associated in parts with both. The individual units of the data processing device can be embodied as separate units or form a single physical unit.

Another embodiment relates to a data processing device, which is configured for performing the method.

With regard to a detailed description and/or advantages of individual aspects of the data processing device, reference is made to the statements made in relation to the method, which can be applied analogously to the device.

Furthermore, an embodiment relates to an X-ray system including:
an X-ray detector which is configured for acquiring X-ray image data and decay image data, and
a data processing device.

The X-ray system is an X-ray machine configured for acquiring a plurality of X-ray projections from the same or different projection angles or projection directions. In a further embodiment, the X-ray system can be embodied for example as a computed tomography system, angiography system, projection radiography system or the like. For example, the X-ray system is a computed tomography apparatus having a ring-shaped rotating frame or a C-arm X-ray machine that can be used both for the one and for the other type of acquisition. The X-ray image projections can be generated, e.g., during an, in particular continuous, rotational movement of an acquisition unit including an X-ray radiation source and an X-ray detector cooperatively interacting with the X-ray radiation source. Alternatively, a plurality of X-ray image projections are acquired in one projection direction while cooperatively interacting X-ray radiation source and X-ray detector are not moved. An X-ray detector for a computed tomography apparatus is, for example, a linear detector having a plurality of lines. An X-ray detector for a C-arm X-ray machine is, for example, a flat-panel detector. Within this approach, the X-ray detector can be embodied both as integrating and as counting.

Integrating X-ray detectors in use today are based mainly on scintillators, made of CsJ for example, that convert, for example, X-ray radiation into comparatively low-energy radiation, for example, visible light. This light is converted into electrical charge in arrays of photodiodes. These are then read out, usually row by row, via active control elements. The basic layout encompassed by said so-called indirect-converting X-ray detectors has a scintillator, an active readout matrix made of amorphous silicon or embodied in CMOS technology having a plurality of pixel elements (with photodiode and switching element) and drive and readout electronics (see, for example, M. Spahn, "Flat detectors and their clinical applications", Eur Radiol. (2005), 15: 1934-1947). Integrating X-ray detectors do not discriminate the incident radiation according to its quantum energy.

According to a preferred development, the X-ray detector is an energy-selective, i.e. energy-resolving, X-ray detector.

This facilitates the acquisition of decay image data or, as the case may be, enables the same simultaneously with the X-ray image acquisition.

Energy-selective is to be understood in this context as spectrally resolving or spectrally separating. Energy-selective detectors are configured for classifying incident radiation quanta according to their quantum energy. These detectors have the advantage that they are suitable for the simultaneous generation of at least two projection datasets that are different in terms of their quantum energy distribution. Energy-selective detectors are, for example, quantum-counting detectors or two-layer detectors. A quantum-counting detector is typically a directly converting detector that converts an incident radiation quantum by suitable detector material directly into an electrical signal. Quantum-counting detectors can be operated as energy-resolving, the energy resolution being selectable by a technique known as binning. In other words, it is possible to specify arbitrary energy ranges in respect of which incident X-ray quanta can be classified. The at least two projection datasets are in each case formed by signals within one or more energy ranges. Suitable detector materials for quantum-counting detectors are in particular the semiconductors cadmium telluride, cadmium zinc telluride or gallium arsenide or, in the case of a flat-panel detector, amorphous selenium or the like. Quantum-counting, energy-selective X-ray detectors are not limited in their applicability for these embodiments. A two-layer detector, also known as a dual- or double-layer detector, is embodied to split the incident radiation spectrum into a low-energy and a high-energy component. For that purpose, the dual-layer detector is composed of two layers. One detector layer facing toward the X-ray radiation source measures low-energy radiation quanta of the incident radiation and allocates the measured signals to the first projection dataset. This layer is penetrated by high-energy radiation. Photons exhibiting higher quantum energy are measured in the detector layer arranged thereunder or therebehind, i.e., facing away from the X-ray radiation source, and are assigned to the second projection dataset. Typically, both detector layers include a scintillator, the dual-layer detector consequently being an indirectly converting detector. Crystals such as cesium iodide or cadmium tungstate, or ceramic substances such as gadolinium oxysulfide or the like, for example, are utilized as scintillation material. Dual-layer detectors are particularly suitable when there is no or negligible overlap between characteristic energy of the radioactive decay and the expected X-ray spectrum.

BRIEF DESCRIPTION OF THE DRAWINGS

The above-described characteristics, features and advantages, as well as the manner in which these are achieved, will become clearer and more readily understandable in connection with the following description of the exemplary embodiments, which are explained in more detail with reference to the drawings. No limitation of the invention to said exemplary embodiments is implied by this description. In the drawings.

DETAILED DESCRIPTION

Figure 1:
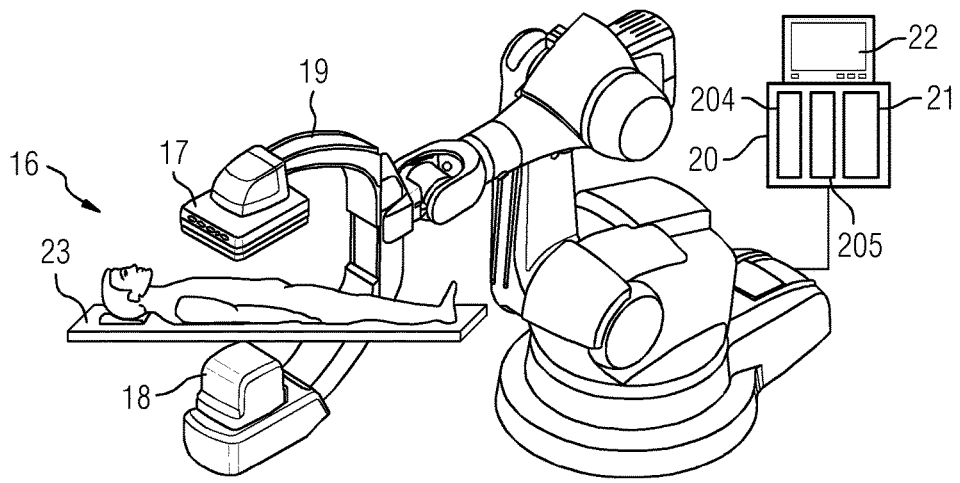
FIG. 1 shows an X-ray system including a data processing device in an exemplary embodiment.

FIG. 1 shows an X-ray system 16 including a data processing device 20 in an exemplary embodiment. The X-ray system 16 has an X-ray tube 18 and an X-ray detector 17, jointly mounted on a C-arm 19, for example, and a high-voltage generator for generating the tube voltage (not shown). The X-ray detector 17 is formed by a flat-panel image detector. Such a flat-panel image detector may find application, e.g., in X-ray systems for interventional procedures, e.g., in cardiology, in radiology as well as in surgery or in the checking of a radiotherapy planning protocol, and in radiotherapy monitoring in brachytherapy or mammography. In addition to being used as a flat-panel detector, an X-ray detector 17 can also be used as a curved line detector, e.g., in computed tomography. The detector can be embodied as an integrating or as a counting X-ray detector, in particular as a digital, counting, energy-discriminating X-ray detector. The X-ray system 16 further includes a data processing device 20, a system control unit 21 typically integrated therein, and a patient table 23. Biplane systems (having two C-arms) are likewise utilized in interventional radiology. In this context, the method according to one embodiment is then performed separately for each X-ray tube detector combination on account of the different projection directions. In computed tomography, the correction method according to an embodiment can basically be performed for each individual projection angle. In order to assure an optimal correction, correction image data is determined for each angular increment by which the scanner advances during the acquisition of X-ray image data, and said correction image data is set against the corresponding X-ray image data. Due to the continuous X-ray radiation employed in computed tomography, it may, however, make more sense in practice to acquire X-ray image data over a specific angular range, e.g. 360°, in the first instance, in the form of individual projections in different projection directions, and subsequently to acquire decay image data over the same angular range, which data then serves as a basis for determining correction image data. In this alternative embodiment, both acquisition period and time window include the recording of a plurality of projections. The data processing device 20 in the form of a computer includes a display unit 22, for example to allow the graphical display of corrected X-ray image data, for example of result images, or for displaying a user interface for a user. The display unit 22 can be an LCD, plasma or OLED screen. The display unit 22 can furthermore be a touch-sensitive screen via which a user can make inputs to the correction method that is to be performed (e.g., via the screen the user can enter details concerning the radioactive material which is present in or on the examination subject, e.g. details concerning the material itself, its mass and/or the time of application). The system control unit 21 is configured for generating control commands, e.g., for the data acquisition for the X-ray system 16, and for transferring the same to the X-ray system. To that end, the data processing device 20 maintains a connection to the X-ray tube 18 and/or to the C-arm 19. The data processing device 20 is also connected for data exchange purposes to the X-ray detector 17. To that end, the data processing device 20 includes an interface unit 204 that is embodied for capturing raw image data from the X-ray detector 17 for further processing by the data processing device 20. From the captured raw image data, the data processing device 20 can produce X-ray image data on the one hand and decay image data on the other. The data processing device 20 is configured for determining correction image data for the X-ray image data of one acquisition period or of a plurality of acquisition periods and for correcting the X-ray image data based on the correction image data. This correction process includes, in particular, an elimination of information relating to the decay process taking place in or on the examination subject in the X-ray image data for one or more acquisition periods. The data processing device 20 also includes a memory unit 205 in which, for example, decay constants for different radioactive materials can be stored ready for retrieval. Corrected X-ray image data can be transferred from the data processing device 20 to the display unit 22 for visualization. The described connections between the units of the X-ray system 16 can be implemented in the known manner on a hardwired or wireless basis.

The data processing device 20 can cooperatively interact with a computer-readable data medium, in particular in order to perform a method by a computer program containing program code. The computer program can furthermore be stored in retrievable form on a machine-readable medium. In particular, the machine-readable medium can be a CD, a DVD, a Blu-ray Disc, a memory stick or a hard disk. The data processing device 20 can be embodied in the form of hardware or in the form of hardware configured by software. The data processing device 20 is embodied for example as a device called a Field Programmable Gate Array (FPGA) or is an arithmetic logic unit.

In the example shown here, at least one computer program is stored in the memory 205 of the data processing device 20, said computer program performing all the steps of the method when the program is executed on the computer. The computer program for performing the steps of the method is program code. The computer program can furthermore be embodied as an executable file and/or be stored on a different computing system from the data processing device 20. For example, the X-ray system 16 can be configured in such a way that the data processing device 20 loads the computer program for performing the method into its internal working memory via an intranet or via the internet.

The memory 205 of the data processing device 20 is embodied for storing specific information, such as e.g., decay constants, for a plurality of radioactive substances, which information could be relevant in the determining of correction image data. Alternatively, the data processing device 20 maintains a connection to a Radiological Information System (RIS) network in order to retrieve the said information, which in this case can be stored in the RIS network.

In a further embodiment, the X-ray system 16 can be embodied, for example, as a computed tomography system, angiography system, projection radiography system or the like.

Figure 2:
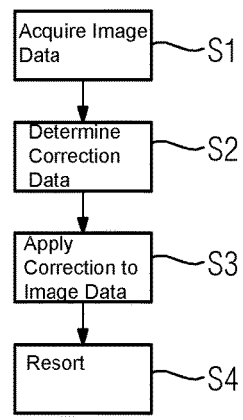
FIG. 2 shows a flowchart of a method in an exemplary embodiment.

FIG. 2 shows a flowchart of method in a first exemplary embodiment. In a first step S1, X-ray image data is acquired for an acquisition period by an X-ray system. Simultaneously, with the X-ray image data acquisition, a radioactive decay takes place in the examination subject, emitting gamma radiation in the process. Said gamma radiation is likewise detected by the X-ray detector and provokes a decay-induced interfering signal in the X-ray image data. In order to minimize or even to eliminate said interfering signal, correction image data is determined in a second step S2. Said data represents the interfering signal in the X-ray image data acquired for the acquisition period. In this exemplary embodiment, the correction image data is based on decay image data relating to the decay process that was likewise acquired by the X-ray detector. The decay image data can be acquired by the X-ray detector concurrently with and/or prior to the acquisition period. The decay image data has a strong temporal relationship with the acquisition period, which is to say that acquisition period and time period for recording the decay image data overlap one another or lie close to one another. By this temporal relationship, it is ensured that the decay process mapped in the decay image data optimally corresponds to the decay process actually taking place during the acquisition period. In order to obtain the correction image data, the decay image data can be subjected to a plurality of further processing steps in order to optimize the information content in relation to the decay process. It can be subjected to a noise minimization function and/or it can be fitted to the characteristic course of the decay process for the radioactive material. In a further step S3, the correction image data is applied to the X-ray image data. As a result, corrected X-ray image data is generated, the decay-induced interfering signal of which has been reduced or removed. For example, the correction image data is subtracted from the X-ray image data, this preferably happening in the image domain whereby, for each image element, i.e., voxel or pixel, the signal contents of the decay image data are deducted from the signal contents of the X-ray image data. The subtraction can also be weighted, e.g., when information concerning the diagnostic relevance or quality of the correction image data has also been obtained during the determination of the correction image data. The weighting can be performed image element by image element, because the decay process generally takes place locally in the X-ray image data or the decay image data, focused at the position at which the radioactive element is disposed in the examination subject. In an optional step S4, the decay image data or the correction image data is resorted to in order to visualize an accumulation of the radioactive material in the examination subject. In other words, the decay image data relating to an interfering signal is also used in this case in the X-ray image data containing the actual image information for the purpose of visualizing image information. In this way, for example, a two-dimensional or three-dimensional activity matrix can be produced for the imaged body region of the examination subject. To that end, the correction image data can be considered or evaluated individually or on an averaged basis. Movements of the X-ray system that may be necessary for this purpose, in particular movements of the X-ray radiation source and the X-ray detector, as well as adjustments to the reconstruction algorithm, are possible without posing any problem to those of ordinary skill in the art within the scope of their competence.

Figure 3:
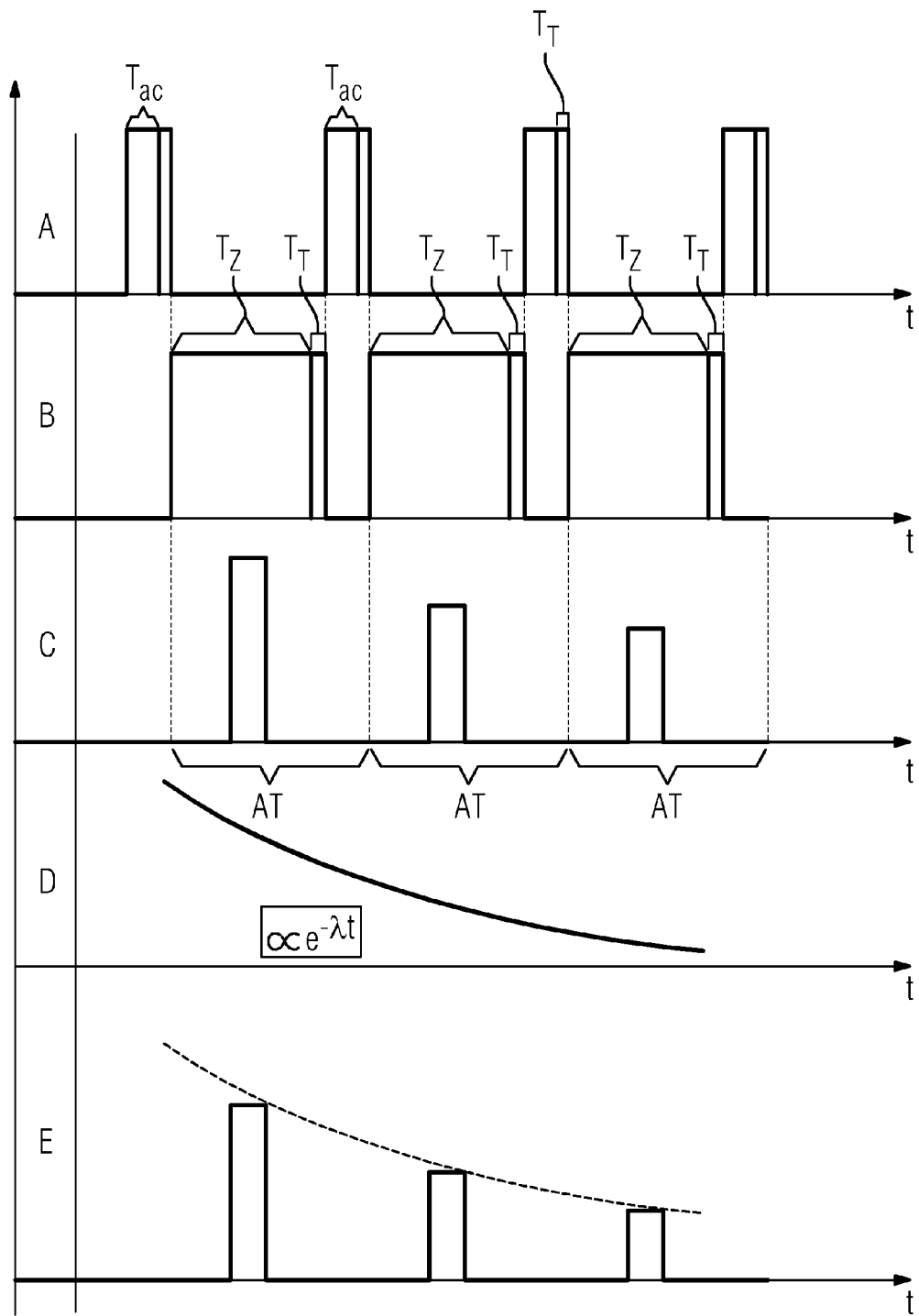
FIG. 3 shows an overview schematic illustrating the method according to a further exemplary embodiment.

FIG. 3 shows an overview schematic to illustrate the method according to a further exemplary embodiment, such as may find application in a perfusion measurement by a C-arm machine and pulsed X-ray radiation. Line A shows the temporally equidistant projection data acquisition. Here, radiation incident on the detector over the temporally recurring acquisition period Tac of, e.g., 10 ms, is detected. Within a time window Tz of, e.g., 78 ms, likewise recurring equidistantly in time, decay image data is acquired for each acquisition period Tac by the X-ray detector. The decay image data is recorded in each case between the acquisition periods, i.e., precisely when the examination subject is not exposed to X-ray radiation. Measured signals are consequently based on the decay process of the radioactive material, possibly including a noise component. Categorically excluded from an image data acquisition are readout times Tt of the X-ray detector of, e.g., 1 ms. In this time, the acquired raw image data is read out from the X-ray detector. The detector is unable to detect incident radiation during this time. The acquired decay image data is now processed further for each acquisition clock cycle AT, i.e., each frame. Optionally, a generally known noise reduction method can be applied in the first instance to the decay projections, for example by performing a smoothing function across the signal contents of adjacent detector elements. In any case, according to this exemplary embodiment, the detected decay signal is fitted or normalized to the length of the acquisition period, Tac. Whereas decay image data was acquired over a time period of, in this case, 78 ms, the X-ray image data relates only to 10 ms in each case. In order to map the decay process within said 10 ms as realistically as possible, the decay image data signal is normalized to the acquisition period, Tac. This is accomplished in this case taking into account the ratio of the duration of the acquisition period, Tac, to the duration of the time window, Tz, for the recording of the decay image data. The intensity (averaged over each decay projection) of the decay image data determined in this way is represented by way of example in line C. Alternatively, the intensity values of the decay image data shown in line C can be arrived at by in each case acquiring within the time windows, Tz, a series of individual decay projections in each case for the duration of an acquisition period, Tac, which are subsequently subjected to an averaging process within the respective time window. This approach enables the standard clock times of the X-ray detector to be maintained. The radioactive decay essentially takes place in accordance with the law of decay, according to which the decay activity decreases exponentially over time. This characteristic curve is shown by way of example in line D. In the event that the radioactive material present in or on the examination subject, the radioactive material quantity, volume and/or the date of application are known, the characteristic course of the radioactive decay taking place at the time of the X-ray examination can be reconstructed. For that purpose, an initial radioactive activity at the commencement of the X-ray examination can be estimated by a functional correlation and on that basis a smoothing of the acquired decay image data can be performed corresponding to the determined course of decay. The smoothed decay image data is shown by way of example in line E and optimally represents the radioactive decay actually taking place within each acquisition clock cycle AT. The correction image data shown in line E can now be applied to the X-ray image data. To that end, the decay image data of each acquisition clock cycle AT is subtracted image element-by-image element from the X-ray image data of the same acquisition clock cycle AT.

Figure 4:
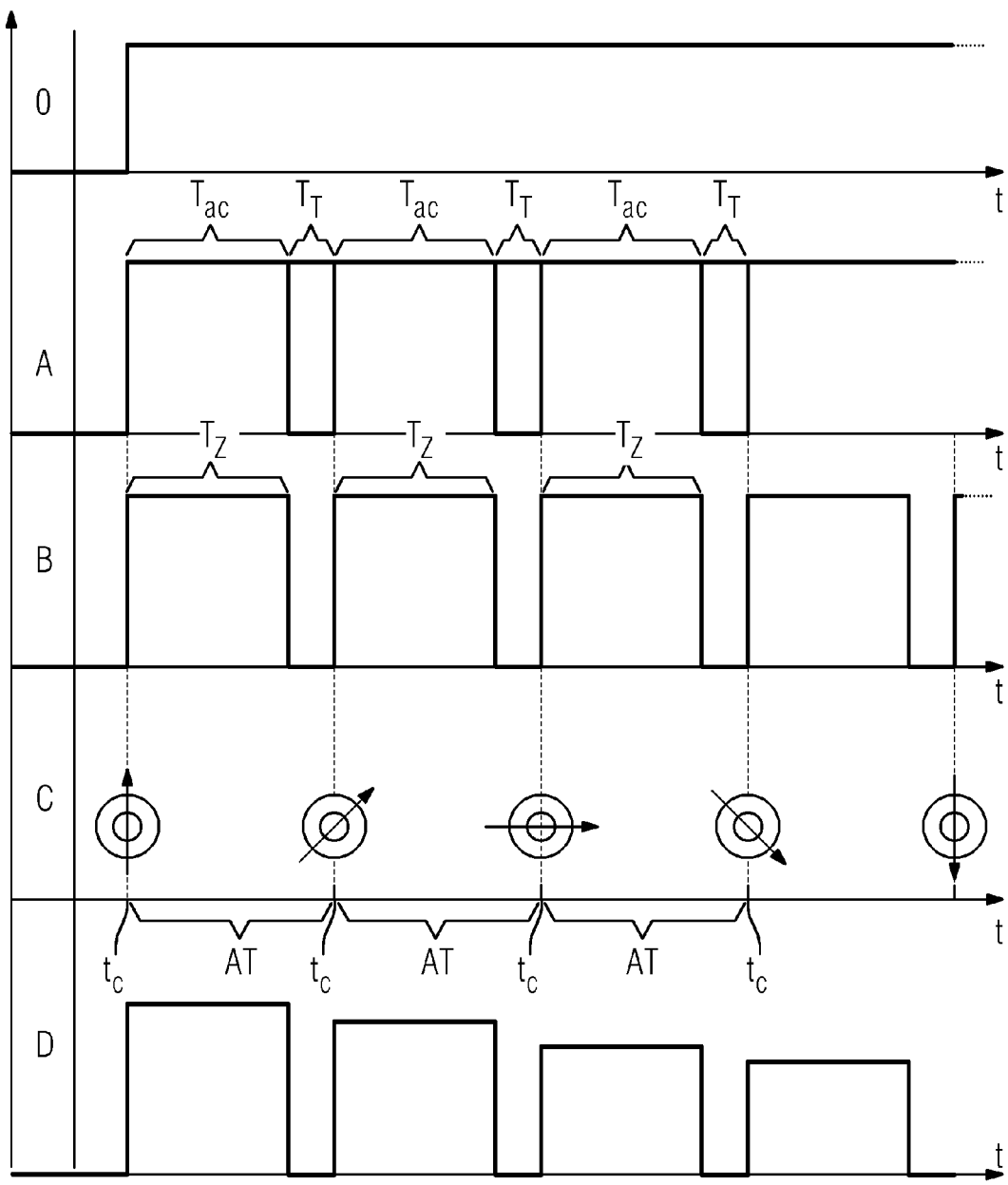
FIG. 4 shows an overview schematic illustrating the method according to a different exemplary embodiment.

FIG. 4 shows an overview schematic of the method according to a further exemplary embodiment. In this case, the method is such as might find application, for example, in conjunction with a computed tomography system that is operated with an energy-selective detector. Line 0 shows the switching state of the X-ray radiation of the computed tomography system that is applied continuously during the X-ray projection acquisition. Line A shows the temporally equidistant projection data acquisition, which is interrupted essentially only by the detector-induced dead times Tt. During the X-ray image acquisition, radiation incident on the detector is detected over the temporally recurring acquisition period, Tac. In computed tomography, each projection is recorded in a different projection direction (i.e., there is a change in direction of the X-ray radiation incident on the examination subject between each projection data acquisition). This can be inferred from line C, where mutually different radiation directions are indicated purely by way of example and not true to scale by the direction of an arrow. The change from one projection direction to the next takes place at time instants, tc, that are likewise equidistant in time. Each acquisition period, Tac, according to line A corresponds in this exemplary embodiment also to a time window, Tz, in which decay image data relating to the radioactive material is acquired, as illustrated in line B. In this exemplary embodiment, the decay image data is incorporated in the acquired X-ray projections (i.e., decay image data is also acquired for each of the aforementioned projection directions). The time windows Tz have the same length or duration as the acquisition periods Tac. In contrast to the detected X-ray radiation, the energy spectrum of the gamma quanta of the radioactive decay is discrete. The decay image data can be identified by evaluating the spectrum of the incident radiation by the energy-selective detector. For example, one or more energy bins of the detector can be set to the quantum energy of the gamma quanta. Count signals in said energy bins are subsequently assigned to the radioactive decay. Corresponding count signals for each time window, Tz, are illustrated in line D. The decay image data can then be subjected to a noise suppression method known per se, (e.g., to a smoothing of the signal contents of the detector across adjacent detector elements). Because the acquisition clock cycle AT in computed tomography turns out to be very short (in this case an assumed 0.25 ms at a revolution time of 0.25 s and 1000 projections per revolution) and the angular increments between two succeeding X-ray projection acquisitions are correspondingly small (0.36° for the assumed 1000 projections per revolution), the decay image data acquired individually for each projection direction for an angular increment of, e.g., 10°, can be averaged in order to determine the correction image data. Likely inaccuracies due to the change in direction or, as the case may be, the temporal alignment are tolerable on account of the comparatively slow progress of the radioactive decay. The decay image data can then be applied to the projection data as correction image data, e.g., by subtracting the decay projections (further processed, as described above, or not) from the corresponding X-ray projections or by initially generating image datasets both from the decay projections and from the X-ray projections and then subtracting these from one another image element by image element.

A further exemplary embodiment (not shown) provides, in the case of an examination by a computed tomography system, initially acquiring decay image data within a time window. The decay image data includes decay projections in a plurality of projection directions, e.g., over an angular range of 360° or more. Said decay image data is used in order to generate a three-dimensional correction image dataset representing the decay process of the radioactive material. X-ray image data including X-ray projections in the same plurality of projection directions is then acquired within an acquisition period over the same angular range. Said X-ray image data is used in order to generate a three-dimensional X-ray image dataset representing the X-ray attenuation distribution of a patient in the examined body region. The correction image data can likewise be corrected taking into account the characteristic course of the decay process with regard to the, in this case, greater temporal offset between correction image data acquisition and X-ray image data acquisition. In view of the relatively slow decay process in comparison with the image data acquisition, good and acceptable results can be achieved even without a correction of said type. Subsequently, a voxel-by-voxel subtraction of the correction image dataset from the X-ray image dataset is carried out in order to eliminate the image information relating to the decay process in the X-ray image data.

This exemplary embodiment furthermore enables the image information relating to the decay process to be selectively shown or hidden, such that both the corrected X-ray image data and the distribution of the radioactive material in the body of a patient can be displayed to the viewer.

Reconstruction steps necessary for performing the method, e.g., forward- or back-projection steps, will be added by those of ordinary skill in the art within the scope of their technical expertise.

Figure 5:
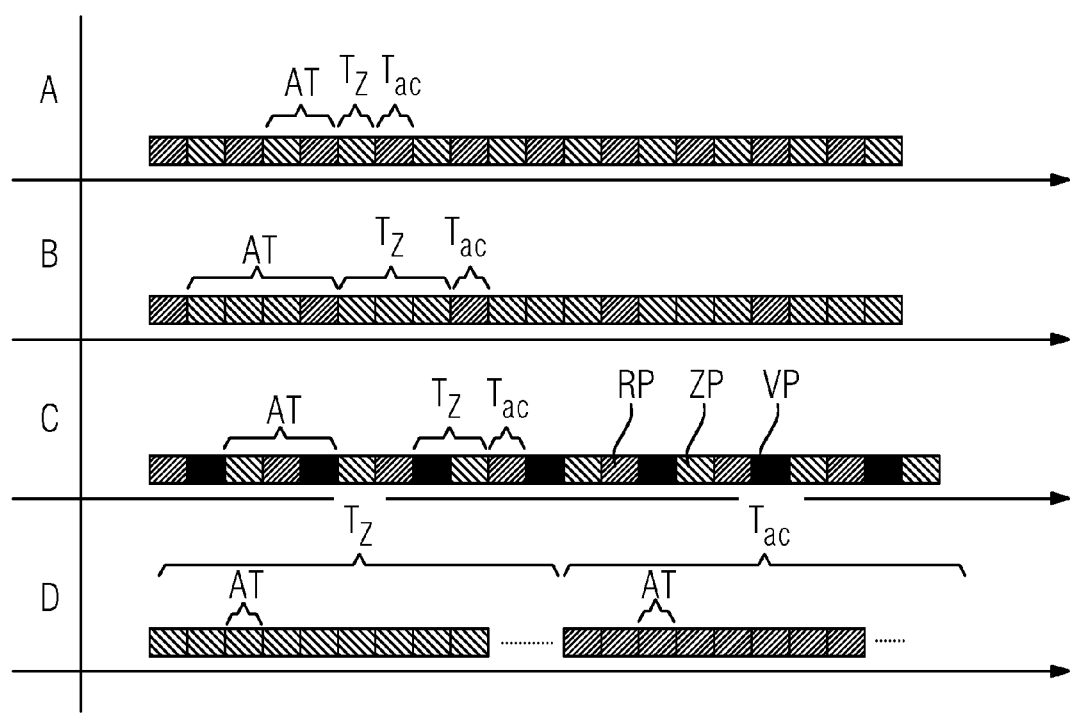
FIG. 5 shows a schematic juxtaposition of exemplary embodiments of the method.

FIG. 5 shows a schematic juxtaposition of exemplary embodiments of the method. Each hatched box shown represents the acquisition time required for recording one projection or frame. This can be an X-ray projection RP, a decay projection ZP or a discarded projection VP. The time characteristic is represented with the aid of the time bar running from left to right. Lines A to C show exemplary embodiments for interventional X-ray systems, while line D shows an exemplary embodiment for a computed tomography system. For interventional X-ray systems, which typically operate with pulsed X-ray radiation, an acquisition clock cycle AT typically takes 4 ms to 100 ms. Typical times for an acquisition clock cycle of a computed tomography system range from 0.1 ms to 0.5 ms. Line A shows the recording of X-ray projections RP in corresponding acquisition periods, Tac, offset in time with respect to the recording of decay projections ZP in corresponding time windows, Tz. The acquisition periods, Tac, and the time windows, Tz, are of equal length. In this exemplary embodiment, one decay projection ZP is acquired per X-ray projection RP and used for determining a correction projection. Line B shows an exemplary embodiment which, in order to correct one X-ray projection RP, takes into account three decay projections ZP that were acquired within an acquisition clock cycle AT immediately prior to the X-ray projection RP. Correspondingly, three decay projections ZP are taken into account in this case for the purpose of correcting the X-ray projection RP of the same acquisition clock cycle AT. Line C shows an exemplary embodiment in which two decay projections ZP are acquired within an acquisition clock cycle AT, although the first of these, as a discarded projection VP, is not taken into account in the correction of the associated X-ray projection RP. The discarded projection VP is discarded because the change from one acquisition clock cycle AT to the next in the case of pulsed X-ray radiation is accompanied by an abrupt drop in incident radiation intensity, which can manifest itself in the form of artifacts during the detection of gamma quanta of the decay process directly after the change. Line D shows an exemplary embodiment in which a plurality of decay projections ZP are first acquired in different projection directions within a time window, Tz, by continuous X-ray radiation and only thereafter a plurality of X-ray projections RP are acquired in an acquisition period, Tac, for the same projection directions. The decay projections ZP are converted into a correction image dataset, the X-ray projections RP into an X-ray image dataset, and the one is then subtracted from the other.

Although the invention has been illustrated in greater detail on the basis of the preferred exemplary embodiment, the invention is not limited by the disclosed examples and other variations can be derived herefrom by those of ordinary skill in the art without leaving the scope of protection of the invention. In particular, features of the described exemplary embodiments can be interchanged among one another where this is technically possible and beneficial.

It is intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A method for correcting X-ray image data of an examination subject, the X-ray image data acquired for an acquisition period by an X-ray detector of an X-ray system simultaneously with a decay process of a radioactive material taking place in or on the examination subject, wherein the X-ray image data comprises information relating to an X-ray attenuation distribution of the examination subject and information relating to the decay process, said method comprising:
   determining correction image data representing the information relating to the decay process in the X-ray image data for the acquisition period, and
   generating corrected X-ray image data for the acquisition period using the X-ray image data and the correction image data.

2. The method as claimed in claim 1, wherein the correction image data is determined for a time window that precedes, is concurrent with, or precedes and is concurrent with the acquisition period.

3. The method as claimed in claim 2, wherein the time window precedes the acquisition period and has a multiple of the length of the acquisition period.

4. The method as claimed in one of claim 3, wherein the time window lies between two succeeding acquisition periods.

5. The method as claimed in one of claim 2, wherein the time window lies between two succeeding acquisition periods.

6. The method as claimed in claim 5, wherein determining of the correction image data comprises determining an acquisition of decay image data by the X-ray detector.

7. The method as claimed in claim 2, wherein determining of the correction image data comprises determining an acquisition of decay image data by the X-ray detector over an entire duration of the time window.

8. The method as claimed in claim 7, wherein, in order to determine the correction image data, the decay image data is normalized to a duration of the acquisition period.

9. The method as claimed in claim 7, wherein, in order to determine the correction image data, the decay image data is normalized to a duration of the acquisition period.

10. The method as claimed in claim 9, wherein the correction image data is determined taking into account a characteristic course of the decay process for the radioactive material.

11. The method as claimed in claim 1, wherein determining of the correction image data comprises determining an acquisition of decay image data by the X-ray detector.

12. The method as claimed in claim 11, wherein, in order to determine the correction image data, the decay image data is normalized to a duration of the acquisition period.

13. The method as claimed in claim 11, wherein the characteristic energy spectrum of the decay process of the radioactive material is taken into account during the acquisition of the decay image data.

14. The method as claimed in claim 11, wherein determining of the correction image data comprises determining an acquisition of decay image data by the X-ray detector over an entire duration of the time window.

15. The method as claimed in claim 1, wherein the correction image data is determined taking into account a characteristic course of the decay process for the radioactive material.

16. The method as claimed in claim 1, which also comprises determining a distribution of the radioactive material on or in the examination subject on the basis of the decay image data or the correction image data.

17. A non-transitory machine-readable data medium on which a computer program is stored, the computer program executable by a processor, the machine-readable data medium comprising the computer program for:
   determining correction image data representing a decay process of radioactive material as an artifact in X-ray image data for an acquisition period, and
   generating corrected X-ray image intensities for the acquisition period using the X-ray image data and the correction image data.

18. A data processing device comprising:
   a memory configured to store instructions;
   a processor configured, by the instructions, to
   determine correction image data representing information relating to a decay process of radioactive material in X-ray image data for an acquisition period, and
   generate corrected X-ray image data for the acquisition period using the X-ray image data and the correction image data.

19. An X-ray system comprising:
   an X-ray detector configured for acquiring X-ray image data and decay image data, and
   a data processing device configured to determine correction image data representing information relating to a decay process of radioactive material in X-ray image data for an acquisition period, and generate corrected X-ray image data for the acquisition period using the X-ray image data and the correction image data.

20. The X-ray system as claimed in claim 19, wherein the X-ray detector is an energy-selective X-ray detector.

* * * * *